United States Patent
Schneider et al.

(10) Patent No.: US 10,226,370 B2
(45) Date of Patent: Mar. 12, 2019

(54) STENTS AND CATHETERS HAVING IMPROVED STENT DEPLOYMENT

(71) Applicant: Covidien LP, Mansfield, MA (US)

(72) Inventors: Lucas Tradd Schneider, Plymouth, MN (US); Bryan Matthew Ladd, Minneapolis, MN (US); Richard Kusleika, Eden Prairie, MN (US); Richard Kravik, Champlin, MN (US); Sandra Vreeman, Circle Pines, MN (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 15/235,377

(22) Filed: Aug. 12, 2016

(65) Prior Publication Data

US 2016/0361186 A1     Dec. 15, 2016

Related U.S. Application Data

(63) Continuation of application No. 13/937,820, filed on Jul. 9, 2013, which is a continuation of application No. 12/556,997, filed on Sep. 10, 2009.

(Continued)

(51) Int. Cl.
*A61F 2/95* (2013.01)
*A61F 2/966* (2013.01)
(Continued)

(52) U.S. Cl.
CPC .............. *A61F 2/966* (2013.01); *A61F 2/844* (2013.01); *A61F 2/95* (2013.01); *A61F 2/958* (2013.01);
(Continued)

(58) Field of Classification Search
CPC combination set(s) only.
See application file for complete search history.

(56) References Cited

U.S. PATENT DOCUMENTS

| 5,234,457 A | 8/1993 | Andersen |
| 5,445,646 A | 8/1995 | Euteneuer et al. |

(Continued)

FOREIGN PATENT DOCUMENTS

| CN | 2605866 | 3/2004 |
| CN | 101234047 | 8/2008 |

(Continued)

OTHER PUBLICATIONS

Communication pursuant to Article 94(3) EPC from counterpart European Application No. 09741070.8, dated Jul. 28, 2016, 4 pp.

(Continued)

*Primary Examiner* — Paul B Prebilic
(74) *Attorney, Agent, or Firm* — Shumaker & Sieffert, P.A.

(57) ABSTRACT

An implant delivery system and method comprises an implant, for example, a stent, and a delivery catheter. The stent has a scaffold with a coating or a shell that retains the scaffold in a collapsed configuration. The coating or shell is made of a material that dissolves or biodegrades upon exposure to a dissolution or biodegradation media. The stent is used with an implant delivery system which has a catheter with a catheter, wherein the stent is mounted on the catheter shaft. The catheter shaft is configured to be withdrawn through the patient's vessel when the scaffold is in its expanded configuration. Advantageously, the implant is thereby prevented from changing length during implant delivery and implant deployment.

23 Claims, 7 Drawing Sheets

Related U.S. Application Data (60) Provisional application No. 61/095,766, filed on Sep. 10, 2008.

(51) Int. Cl.
    *A61F 2/958* (2013.01)
    *A61F 2/962* (2013.01)
    *A61F 2/844* (2013.01)

(52) U.S. Cl.
    CPC ...... *A61F 2/962* (2013.01); *A61F 2002/9505* (2013.01); *A61F 2002/9665* (2013.01); *A61F 2210/0004* (2013.01)

(56) References Cited

U.S. PATENT DOCUMENTS

| | | | |
|---|---|---|---|
| 5,510,077 A * | 4/1996 | Dinh | A61F 2/82 264/279 |
| 6,171,295 B1 | 1/2001 | Garabedian et al. | |
| 6,213,995 B1 | 4/2001 | Steen et al. | |
| 6,391,033 B2 | 5/2002 | Ryan | |
| 7,476,214 B2 | 1/2009 | Sydney | |
| 7,648,727 B2 | 1/2010 | Hossainy et al. | |
| 2002/0052640 A1 * | 5/2002 | Bigus | A61F 2/07 623/1.11 |
| 2002/0143392 A1 | 10/2002 | Ryan | |
| 2003/0028173 A1 | 2/2003 | Forsberg | |
| 2003/0114909 A1 | 6/2003 | Clerc et al. | |
| 2003/0215564 A1 | 11/2003 | Heller | |
| 2004/0002751 A1 | 1/2004 | Gilligan | |
| 2004/0024441 A1 | 2/2004 | Bertolino | |
| 2005/0234538 A1 | 10/2005 | Litvack et al. | |
| 2006/0015170 A1 | 1/2006 | Jones | |
| 2006/0030835 A1 | 2/2006 | Sherman et al. | |
| 2006/0212106 A1 | 9/2006 | Weber et al. | |
| 2007/0016280 A1 | 1/2007 | Yacoby et al. | |
| 2007/0173923 A1 * | 7/2007 | Savage | A61F 2/91 623/1.15 |
| 2007/0288088 A1 | 12/2007 | Bureau et al. | |
| 2009/0166913 A1 | 7/2009 | Guo et al. | |

FOREIGN PATENT DOCUMENTS

| | | |
|---|---|---|
| EP | 1955724 | 8/2008 |
| JP | 9-313617 | 12/1997 |
| JP | 2004-313222 | 11/2004 |
| JP | 2005524487 | 8/2005 |
| JP | 503945 | 1/2009 |
| WO | WO9511055 | 4/1995 |
| WO | WO03051425 | 6/2003 |
| WO | WO2006101573 | 9/2006 |
| WO | WO2009085486 | 7/2009 |

OTHER PUBLICATIONS

Notice of Reasons for Rejection, and English translation thereof, from Counterpart Japanese Patent Application No. 2011526968, dated Aug. 20, 2013, 12pp.

Notice of Reasons for Rejection, and English translation thereof, from Counterpart Japanese Patent Application No. 2011526968, dated Apr. 11, 2014, 11 pp.

Notice of Final Rejection and English translation thereof, from Counterpart Japanese Patent Application No. 2011526968, dated Aug. 8, 2014, 5pp.

* cited by examiner

STENTS AND CATHETERS HAVING IMPROVED STENT DEPLOYMENT

CROSS-REFERENCE TO RELATED APPLICATIONS

This application is a continuation of U.S. application Ser. No. 13/937,820, filed Jul. 9, 2013, which is a continuation of U.S. application Ser. No. 12/556,997, filed Sep. 10, 2009, which claims the benefit of U.S. provisional application Ser. No. 61/095,766, filed Sep. 10, 2008, the entire contents of which are incorporated herein by reference in their entirety.

FIELD OF THE INVENTION

The present invention relates to systems for delivering an implant to a site in a body lumen. More particularly, this invention pertains to delivery systems for a vascular implant such as a self-expanding stent.

BACKGROUND OF THE INVENTION

Stents are widely used for supporting a lumen structure in a patient's body. For example, stents may be used to maintain patency of a coronary artery, carotid artery, cerebral artery, femoral artery, other blood vessels including veins, or other body lumens such as the ureter, urethra, bronchus, esophagus, or other passage.

Stents are commonly metallic tubular structures made from stainless steel, Nitinol, Elgiloy, cobalt chrome alloys, tantalum, and other metals, although polymer stents are known. Stents can be permanent enduring implants, or can be bioabsorbable at least in part. Bioabsorbable stents can be polymeric, bio-polymeric, ceramic, bio-ceramic, or metallic, and may elute over time substances such as drugs. Non-bioabsorbable stents may also release drugs over time. Stents are passed through a body lumen in a collapsed state. At the point of an obstruction or other deployment site in the body lumen, the stent is expanded to an expanded diameter to support the lumen at the deployment site.

In certain designs, stents are comprised of tubes having multiple through holes or cells that are expanded by inflatable balloons at the deployment site. This type of stent is often referred to as a "balloon expandable" stent. Stent delivery systems for balloon expandable stents are typically comprised of an inflatable balloon mounted on a two lumen tube. The stent delivery system with stent compressed thereon can be advanced to a treatment site over a guidewire, and the balloon inflated to expand and deploy the stent.

Other stents are so-called "self expanding" stents and do not use balloons to cause the expansion of the stent. An example of a self-expanding stent is a tube (e.g., a coil of wire or a tube comprised of cells) made of an elastically deformable material (e.g., a superelastic material such a nitinol). Some self expanding stents are also comprised of tubes having multiple through holes or cells. This type of stent is secured in compression in a collapsed state to a stent delivery device. At the deployment site, stent compression is released and restoring forces within the stent cause the stent to self-expand to its enlarged diameter.

Other self-expanding stents are made of so-called shape-memory metals. Such shape-memory stents experience a phase change at the elevated temperature of the human body. The phase change results in expansion from a collapsed state to an enlarged state.

A very popular type of self expanding stent is a cellular tube made from self-expanding nitinol, for example, the EverFlex stent from ev3, Inc. of Plymouth, Minn. Cellular stents are commonly made by laser cutting of tubes, or cutting patterns into sheets followed by or preceded by welding the sheet into a tube shape, and other methods.

Another delivery technique for a self expanding stent is to mount the collapsed stent on a distal end of a stent delivery system. Such a system can be comprised of an outer tubular member and an inner tubular member. The inner and outer tubular members are axially slideable relative to one another. The stent (in the collapsed state) is mounted surrounding the inner tubular member at its distal end. The outer tubular member (also called the outer sheath) surrounds the stent at the distal end.

Prior to advancing the stent delivery system through the body lumen, a guide wire is first passed through the body lumen to the deployment site. The inner tube of the delivery system is hollow throughout at least a portion of its length such that it can be advanced over the guide wire to the deployment site. The combined structure (i.e., stent mounted on stent delivery system) is passed through the patient's lumen until the distal end of the delivery system arrives at the deployment site within the body lumen. The deployment system and/or the stent may include radiopaque markers to permit a physician to visualize positioning of the stent under fluoroscopy prior to deployment. At the deployment site, the outer sheath is retracted to expose the stent. The exposed stent is free to self-expand within the body lumen. Following expansion of the stent, the inner tube is free to pass through the stent such that the delivery system can be removed through the body lumen leaving the stent in place at the deployment site.

In prior art devices, high forces may be required to retract the outer sheath so as to permit the stent to self expand. Delivery systems designed to withstand high retraction forces can be bulky, can have reduced flexibility and can have unacceptable failure rates. In addition, due to frictional forces between the stent and the outer sheath in prior art devices the stent may change in length during deployment, either in overall length or locally over regions of the stent. For example, long stents, thin stents, stents with high axial flexibility parallel to the central axis of the stent, or stents with a large amount of expansile force, when compressed in a sheath, tend to change in length as the outer sheath is withdrawn from the inner tubular member. Also, prior art delivery systems can be moved when the implant is partially deployed, resulting in undesirable regional length changes in the implanted device. Changes in stent length during stent deployment can prevent a stent from being properly deployed over the intended treatment area, can compromise stent fracture resistance and can compromise stent fatigue life.

What is needed is a stent delivery system that permits low force and precise delivery of stents without altering the intended length of the stent.

SUMMARY OF THE INVENTION

According to one aspect of the present invention, a stent includes a scaffold and a coating that restrains diametrical expansion of the scaffold. Dissolution or biodegradation of the coating allows the stent to expand or be expanded.

According to another aspect of the present invention, a stent includes a scaffold and a shell that restrains diametrical expansion of the scaffold. Dissolution or biodegradation of the shell allows the stent to expand or be expanded.

According to other aspects of the present invention, an implant delivery system includes a stent with a scaffold and a coating or shell that restrains diametrical expansion of the scaffold and a catheter on which the stent is mounted in a collapsed, restrained state. Upon exposure to dissolution fluid or biodegradation media, dissolution or biodegradation of the coating or shell allows the stent to expand or be expanded.

According to other aspects of the present invention, an implant delivery system includes a stent with a scaffold and a coating that restrains diametrical expansion of the scaffold and an inflatable balloon mounted on the catheter beneath the stent. Upon inflating the balloon the coating or shell is compromised or fractured and the stent self-expands or is further expanded by further inflation of the balloon. Exposure to dissolution fluid or biodegradation media causes fragments of the coating or shell to dissolve or biodegrade.

According to other aspects of the present invention, an implant delivery system includes a stent with a scaffold and a coating that restrains diametrical expansion of the scaffold and a slidable tubular sheath surrounding the catheter and restrained stent. Upon proximal withdrawal of the sheath the coating or shell is exposed to dissolution fluid or biodegradation media and dissolution or biodegradation of the coating or shell allows the stent to expand or be expanded. Exposure to dissolution fluid or biodegradation media causes fragments of the coating or shell to dissolve or biodegrade.

According to yet other aspects of the present invention, an implant delivery system includes a stent with a scaffold and a coating that restrains diametrical expansion of the scaffold, and a slidable tubular sheath surrounding the catheter, an inflatable balloon and a restrained stent. The stent is deployed by proximal withdrawal of the sheath followed by inflation of the balloon to compromise or fracture the coating or shell. The stent then self-expands or is further expanded by further inflation of the balloon. Exposure to dissolution fluid or biodegradation media causes fragments of the coating or shell to dissolve or biodegrade.

In yet another aspect of the present invention, an implant delivery system having a stent with a scaffold and a coating that restrains diametrical expansion of the scaffold is delivered to a treatment site, a slidable tubular sheath surrounding the catheter, an inflatable balloon and a restrained stent, is delivered to a treatment site. At the treatment site, the balloon is inflated until the sliding friction of the stent against the balloon is greater than the sliding friction of the stent against the outer sheath. The outer sheath is then retracted to expose the stent which self expands upon exposure. The stent may be further expanded by further inflation of the balloon.

BRIEF DESCRIPTION OF THE DRAWINGS

The above and further advantages of the invention may be better understood by referring to the following description in conjunction with the accompanying drawings in which.

DETAILED DESCRIPTION

Embodiments that are examples of how inventive aspects in accordance with the principles of the present invention will now be described in more detail with reference to the drawings. It is to be understood that both the foregoing general description and the following detailed description are exemplary and explanatory only and are not restrictive of the broad inventive aspects disclosed herein. It will also be appreciated that the inventive concepts disclosed herein are not limited to the particular stent configurations disclosed herein, but are instead applicable to any number of different stent configurations.

Figure 1A:
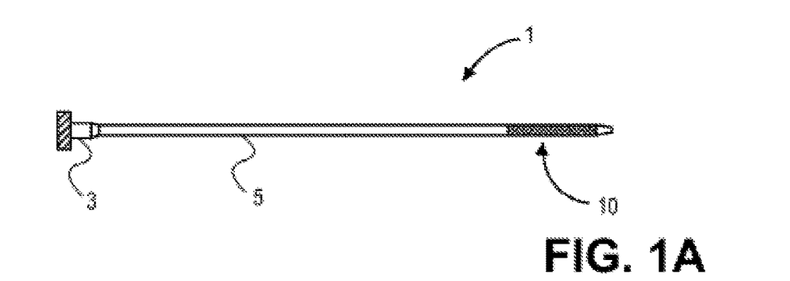
FIG. 1A illustrates a schematic side view of an implant delivery system having features in accordance with the principles of the present disclosure.
Figure 1B:
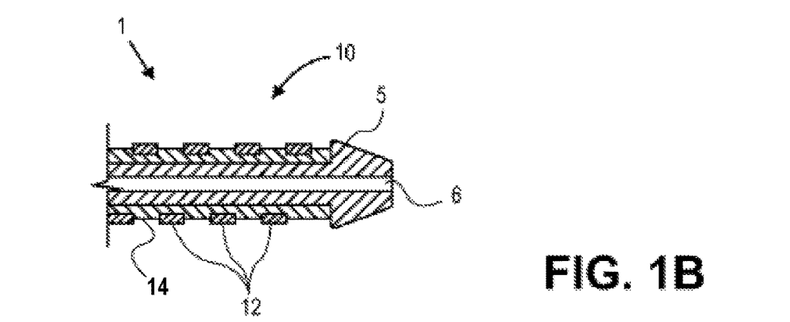
FIGS. 1B, 1C and 2 illustrate schematic cross sectional views of stent and stent implant system embodiments having features in accordance with the principles of the present disclosure.
Figure 1C:
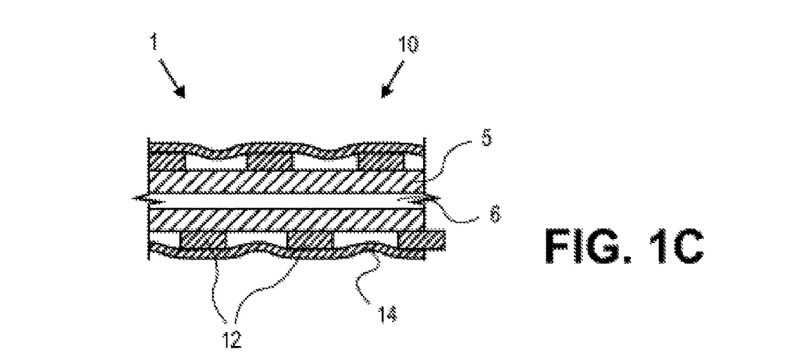

FIGS. 1A and 1B illustrate implant delivery system 1 comprised of stent 10, catheter shaft 5 with hub 3 and guidewire lumen 6 extending through catheter shaft and hub. Catheter shaft 5 is relatively flexible, may be comprised of a polymeric material such as nylon or PEBAX, and may range in length from 60 cm to 300 cm. Catheter outside diameter may range from about 2 Fr to about 10 Fr. Guidewire lumen 6 diameter may be large enough to allow passage of guidewires ranging in diameter from 0.009" to 0.038". Hub 3 is sealingly attached to catheter shaft 5, is adapted to reversibly connect to other medical devices (for example by means of a luer fitting) and may be comprised of polycarbonate. Stent 10 is comprised of scaffold 12 and coating 14. In various embodiments scaffold may be self expanding, balloon expandable, tubular, comprised of cells, comprised of coils, comprised of metals, polymer, ceramics, or other materials, or may have other characteristics. In one embodiment scaffold 12 includes Nitinol tubing having cellular openings and having suitable heat treatment to cause scaffold 12 to self-expand at human body temperatures. Scaffold 12 configurations suitable for the invention include but are not limited to tapered, flared, braided, bifurcated, fracturable, mesh covered, scaffolds comprised of radiopaque markers, and other scaffolds as are known in the art. Long scaffolds are especially suited to the invention. Implant delivery systems 1 for scaffolds having lengths of from 20-400 mm are contemplated. In one embodiment, implant delivery system 1 can deliver and deploy a 30 mm scaffold. In other embodiments, implant delivery system 1 can deliver and deploy a 40 mm, 60 mm, 80 mm, 100 mm, 120 mm, 150 mm, 180 mm, 200 mm, 250 mm, 300 mm or 350 mm scaffold. As shown in FIGS. 1B and 1C, coating 14 may optionally be applied to catheter shaft 5 outer diameter along some or all of the scaffold length and may be applied to at least one of outer surface, inner surface, or through thickness of scaffold 12. In some embodiments coating 14 covers the exposed edges of stent 10 so as to form a smooth exterior coated stent surface. Coating 14, when applied and hardened, maintains stent 10 at an unexpanded diameter and a fixed length prior to stent deployment. Coating 14 may cause stent to adhere directly to inner member. Coating 14 may be comprised of biodegradable materials, or may be comprised of materials that dissolve in the body or in the bloodstream. In some embodiments coating 14 includes sugar, carbowax, polyethylene oxide, poly vinyl alcohol or other materials. Coating 14 may be applied by spray, dip, or other processes to unexpanded stent and allowed to harden, may be applied to expanded stent and allowed to harden after stent is compressed, may be applied to and hardened on expanded stent so as to maintain scaffold in an unexpanded diameter after subsequent stent compression, or may be applied and hardened by other methods.

In some embodiments coating 14 can dissolve or biodegrade over time so as to release the scaffold. In some embodiments coating 14 can dissolve or biodegrade when in contact with blood to allow expansion of scaffold 12. Upon contact with dissolution or biodegradation causing media, scaffold release times of 0.5 to 300 seconds are contemplated. In one embodiment, scaffold release time is approximately 1 second. In other embodiments, scaffold release time is approximately 2, 5, 10, 20, 30, 45, 60, 90, 120, 150, 180 or 240 seconds. In some embodiments a change in scaffold 12 length of less than 10% upon expansion from a contracted to an expanded configuration is contemplated. In other embodiments, scaffold 12 length change upon expansion from a contracted to an expanded configuration is less than 9%, 8%, 7%, 6%, 5%, 4%, 3%, 2%, or 1%.

Coating 14 may be comprised of bioactive materials such as antirestenotic agents, anti-inflammatory agents, antithrombotic agents, antiatheromatic (antiatheroma) agents, antioxidative agents, or other agents. Bioactive coating materials may be released from the coating into surrounding tissue or blood and may have a diagnostic or therapeutic action on tissue or blood.

An exemplary method of using a stent 10 with implant delivery system 1 is now described. A guidewire is advance into a patient's femoral artery using known techniques, through a patient's vessel and past a treatment site. Stent 10 is loaded onto implant delivery system 1 and introduced over the guidewire into the patient's vessel. Stent 10 is restrained from expanding by coating 14. The stent and implant delivery system combination is advanced over the guidewire and through the patients vessel until stent 10 is located at a treatment site, for example within a stenosis in a femoral artery. Stent 10 is deployed by allowing coating 14 to dissolve or to biodegrade thereby allowing scaffold 12 to self-expand. Catheter shaft 5 is then withdrawn through the patient's vessel and out of the patient's body. Any of coating that is pinned between scaffold and the vessel, attached to scaffold, or which embolizes from the treatment site dissolves or biodegrades over time. Scaffold 10 does not change length upon deployment because the scaffold is immobilized on catheter shaft 5 by coating 14 during delivery to the treatment site and because there is no sheath to draw past the stent during deployment.

Figure 2:
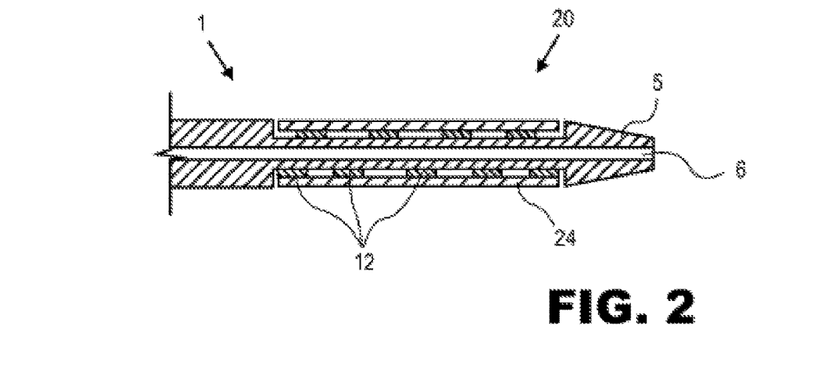

FIG. 2 illustrates implant delivery system 1 comprised of stent 20, catheter shaft 5 with hub (not shown) and guidewire lumen 6 extending through catheter shaft and hub. Stent 20 includes scaffold 12 and shell 24. Shell 24 surrounds scaffold 12 and may form a smooth exterior surface over stent 20. Shell 24 maintains stent 20 at an unexpanded diameter prior to stent deployment and may be comprised of biodegradable materials, or may be comprised of materials that dissolve in the body or in the bloodstream. In some embodiments shell 24 includes sugar, carbowax, polyethylene oxide, poly vinyl alcohol, poly lactic acid (PLA), poly glycolic acid (PGA), poly lactic glycolic acid (PLGA), poly (ε-caprolactone) copolymers, polydioxanone, poly(propylene fumarate) poly(trimethylene carbonate) copolymers, polyhydroxy alkanoates, polyphosphazenes, polyanhydrides, poly(ortho esters), poly(amino acids), or "pseudo"-poly(amino acids).

The resorption or dissolution time of shell 24 can be varied by varying the ratio of constituent materials or by other means. The shell material may be axially or biaxially oriented or may have other structure. Shell 24 may be comprised of tubing into which scaffold 12 is inserted, or of film which is wrapped around compressed scaffold, or other structures, and may be applied by other application methods. Shell may be slit, perforated, have a high ability to stretch, may soften abruptly or substantially when heated to near body temperature, or have other characteristics to aid with shell fracture during scaffold expansion.

In some embodiments shell 24 can dissolve or biodegrade over time so as to release scaffold. In some embodiments shell 24 can dissolve or biodegrade when in contact with blood to allow expansion of scaffold 12. Upon contact with dissolution or biodegradation causing media, scaffold release times of 0.5 to 300 seconds are contemplated. In one embodiment, the scaffold release time is approximately 1 second. In other embodiments, the scaffold release time is approximately 2, 5, 10, 20, 30, 45, 60, 90, 120, 150, 180 or 240 seconds. In some embodiments a change in scaffold 12 length of less than 10% upon expansion from a contracted to an expanded configuration is contemplated. In other embodiments, scaffold 12 length change upon expansion from a contracted to an expanded configuration is less than 9%, 8%, 7%, 6%, 5%, 4%, 3%, 2% or 1%.

Shell 24 may be comprised of bioactive materials such as antirestenotic agents, anti-inflammatory agents, antithrombotic agents, antiatheromatic (antiatheroma) agents, antioxidative agents, or other agents. Bioactive coating materials may be released from the coating into surrounding tissue or blood and may have a diagnostic or therapeutic action on tissue or blood.

Figure 3A:
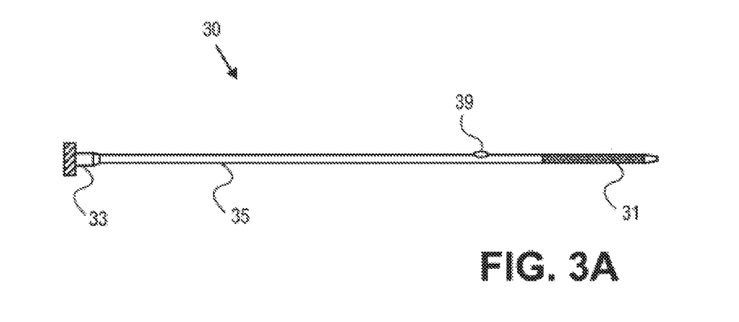
FIGS. 3A to 3C, 4, and 5A to 5D illustrate schematic cross sectional views of implant delivery systems having features in accordance with the principles of the present disclosure.
Figure 3B:
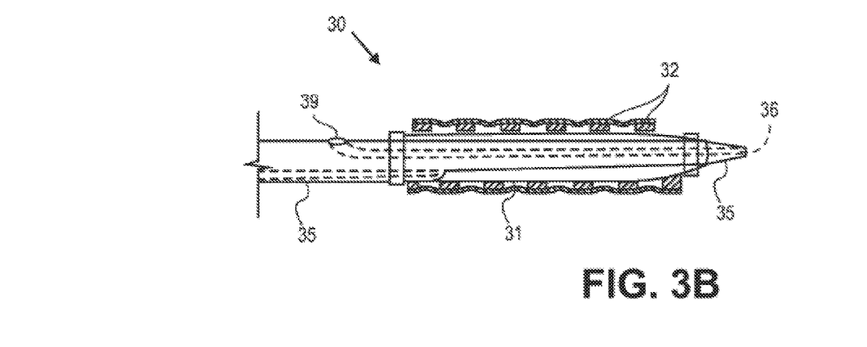
Figure 3C:
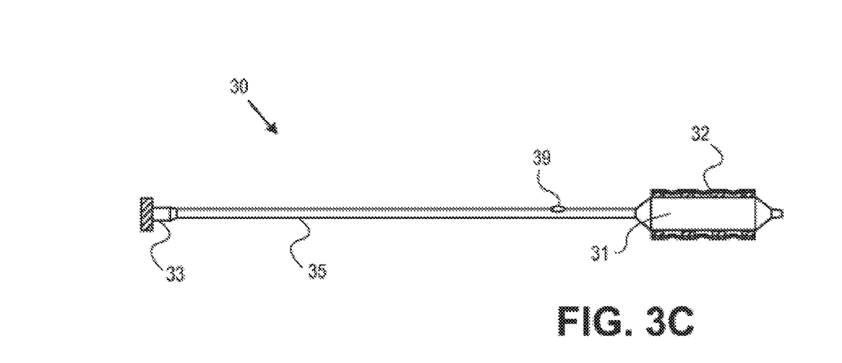

An exemplary method of using a stent 20 with implant delivery system 1 is now described. A guidewire is advance into a patient's femoral artery using known techniques, through a patient's vessel and past a treatment site. Stent 20 is loaded onto implant delivery system 1 and introduced over the guidewire into the patient's vessel. Stent 20 is restrained from expanding by shell 24. The stent and implant delivery system combination is advanced over the guidewire and through the patients vessel until stent 20 is located at a treatment site, for example within a stenosis in a carotid artery. Stent 20 is deployed by allowing shell 24 to dissolve or to biodegrade thereby allowing scaffold to self-expand. Shell may fracture upon expansion of scaffold, and such fracture may be assisted by preplaced slits, slots, local thinning of wall thickness of shell, or other means. Catheter shaft 5 is then withdrawn through the patient's vessel and out of the patient's body. Any of shell 24 that is pinned between scaffold and the vessel, attached to scaffold, or which embolizes from the treatment site dissolves or biodegrades over time. Scaffold 12 does not change length on deployment because the scaffold is immobilized on catheter shaft 5 during delivery to the treatment site and because there is no sheath to draw past the stent during deployment FIGS. 3A to 3C illustrate an example of a Rapid Exchange (RX) delivery system 30 comprised of stent 32, catheter shaft 35 having balloon inflation lumen (not shown), guidewire lumen 36, guidewire lumen exit skive 39 and inflation hub 33, and balloon 31. Catheter shaft 35 is relatively flexible, may be comprised of a polymeric material such as nylon or PEBAX, and may range in length from 60 cm to 300 cm. Catheter shaft 35 outside diameter may range from about 2 Fr to about 10 Fr. Guidewire lumen 36 diameter may be large enough to allow passage of guidewires ranging in diameter from 0.009" to 0.038". Hub 33 is sealingly attached to catheter shaft 35, is adapted to reversibly connect to other medical devices (for example by means of a luer fitting) and may be comprised of polycarbonate. Balloon 31 is sealingly attached at both proximal and distal ends to catheter shaft 35 and may be comprised of biaxially oriented nylon, polyester, Pebax, polyolefin, or other materials. Stent 32 may be comprised of stents 10, 20 or other stents, is shown in an unexpanded configuration in FIGS. 3A and 3B and in an expanded configuration in FIG. 3C. Stent 32 is deployed by connecting an inflation device (not shown) to hub 33 and pressurizing balloon inflation lumen with fluid or gas so as to expand balloon 31 thereby expanding stent 32. In some embodiments stent 32 is fully expanded into contact with vessel wall by expansion of balloon 31.

When balloon 31 is expanded beneath stent 10, the restraining force of coating 14 is overcome by balloon pressure and the coating fractures, allowing stent 10 to expand. When balloon 31 is expanded beneath stent 20, the restraining force of shell 24 is overcome by balloon pressure and the shell fractures, allowing stent 20 to expand.

An exemplary method of using stent 32 with delivery system 30 is now described. A guidewire is advanced into a patient's femoral artery using known techniques, through a patient's vessel and past a treatment site. A stent 32 (for example stent 10, 20) is loaded onto implant delivery system 30 and introduced over the guidewire into the patient's vessel. The stent and implant delivery system combination is advanced over the guidewire and through the patient's vessel until the stent is located at a treatment site, for example within a stenosis in a carotid artery. Stent 10, 20 is deployed by inflating balloon 31 thereby causing coating 14 or shell 24 to fracture and stent to expand. Catheter 35 is then withdrawn through the patient's vessel and out of the patient's body. Any of coating or shell that is pinned under scaffold, or which embolizes, dissolves/degrades over time. Stent 10, 20 does not change length on deployment because the stent is immobilized on catheter shaft 35 during delivery to the treatment site and because there is no sheath to draw past the stent during deployment.

Figure 4:
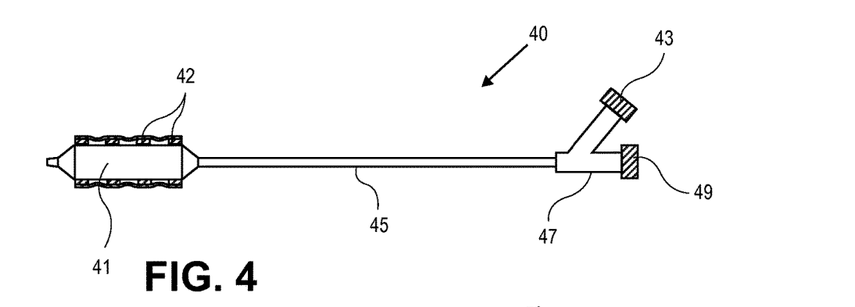

FIG. 4 illustrates an example of an Over The Wire (OTW) delivery system 40 comprised of stent 42, catheter shaft 45 having balloon inflation lumen (not shown), guidewire lumen (not shown) and manifold 47, and balloon 41. Manifold 47 includes guidewire lumen exit port 49 and inflation hub 43. Catheter shaft 45, guidewire lumen, balloon 41, and inflation hub 43 have substantially the same construction, dimensions, and function as catheter shaft 35, guidewire lumen 36, balloon 31, and inflation hub 33 described above in conjunction with FIGS. 3A to 3C. Manifold 47 is sealingly attached to catheter shaft 45 and may be comprised of polycarbonate. Guidewire lumen exit port 49 and inflation hub 43 are adapted to reversibly connect to other medical devices (for example by means of a luer fitting). (for example stent 10, 20), Stent 42 may be comprised of stents 10, 20 or other stents and is shown in an expanded configuration in FIG. 4. Stent 42 is deployed by connecting inflation device (not shown) to hub 43 and pressurizing balloon inflation lumen with fluid or gas so as to expand balloon 41 thereby expanding stent 42. In some embodiments stent 42 is fully expanded into contact with vessel wall by expansion of balloon 41.

The methods of using and the benefits of using Over The Wire (OTW) delivery system 40 are substantially the same as those described above for Rapid Exchange (RX) delivery system 30.

Figure 5A:
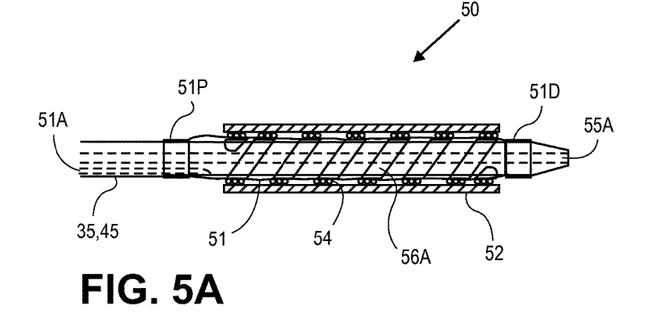
Figure 5B:
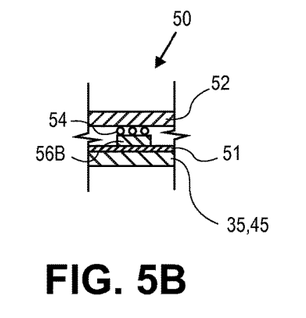
Figure 5C:
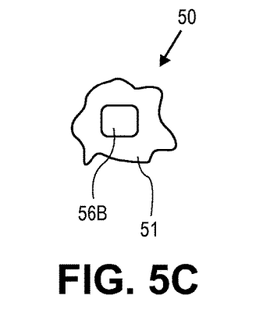
Figure 5D:
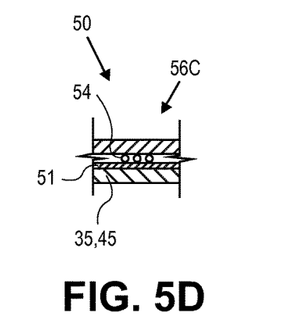

FIGS. 5A, 5B, 5C and 5D illustrate further embodiments of implant delivery systems having features in accordance with the principles of the present disclosure. FIG. 5A illustrates implant delivery system 50 comprised of implant delivery system 30, 40 with modifications to the distal balloon containing portion of implant delivery system 30, 40. Proximal region of system 50 includes catheter shaft 35, 45 having balloon inflation lumen 51a and guidewire lumen 55a, inflation hub 33, 43 (not shown) and either guidewire lumen exit skive 39 (not shown) in catheter shaft 35 or manifold 47 (not shown) attached to catheter shaft 45 as described above for systems 30, 40. Distal region of system 50 includes catheter shaft 35, 45, balloon 51, stent 52, band 56a and adhesive 54. Balloon 51 is sealingly attached to catheter shaft 35, 45 at proximal and distal bonds 51p, 51d and may be comprised of compliant, semi compliant, non-compliant, or low pressure balloon materials and may be comprised of biaxially oriented nylon, polyester, Pebax, polyolefin, or other materials. In some embodiments balloon 51 includes highly elastic materials such as polyurethane elastomers.

Stent 52 may be comprised of stent 10, stent 20, or any stent to which adhesive 54 can bond. For example, stent 54 configurations suitable for the invention include but are not limited to cellular stents, fracturable stents, coil stents, covered stents, stent grafts, mesh covered stents, tapered stents, flared stents, braided stents, bifurcation stents, and other stents as are known in the art. Long stents are especially suited to the invention. Implant delivery systems 50 for stents having lengths of from 20 to 400 mm are contemplated. In one embodiment, a stent delivery system 50 can deliver and deploy a 30 mm stent. In other embodiments, a stent delivery system 50 can deliver and deploy a 40 mm, 60 mm, 80 mm, 100 mm, 120 mm, 150 mm, 180 mm, 200 mm, 250 mm, 300 mm or 350 mm stent.

Band 56a is attached to catheter shaft 35, 45 by friction fit and may be comprised of materials such as metal, Elgiloy, platinum, platinum alloy, nickel-titanium alloy, engineering polymer, liquid crystal polymer, polyester, nylon, or other materials. Edges of band are rounded so as to not promote balloon burst upon balloon inflation. Band 56a sandwiches balloon 51 between band and catheter shaft. Band is configured to allow inflation of the portion of balloon 51 that does not underlie band 56a. In one embodiment band 56a takes the form of a coiled ribbon. In another embodiment, outer surface of catheter 35, 45 has a groove therealong to receive band 56a. Adhesive 54 attaches stent 52 to band 56a and may be comprised of biodegradable or dissolvable materials such as poly lactic acid (PLA), poly glycolic acid (PGA), or poly lactic glycolic acid (PLGA), or may be comprised of EVA, polyurethane, nylon, or other materials. In some embodiments adhesive extends into openings through wall thickness of stent 52.

In an alternate embodiment (FIGS. 5B and 5C), band 56b includes one or more patches or islands of material having circular, oval, irregular, or other shape and is further comprised of one or more of the materials used to construct band 56a. Band 56b is bonded to balloon 51, and balloon 51 is locally bonded to catheter shaft 35, 45 in the region underlying band 56b by means of heat, adhesive, or other means. Local bonds of balloon 51 to catheter shaft 35, 45 are arranged in a pattern that allows flow to inflate unbonded portion of balloon. In yet another embodiment (FIG. 5D), balloon is locally bonded to catheter shaft 35, 45 by means of heat, adhesive, or other means over a patch or island having circular, oval, irregular, or other shape and band 56c includes the bonded region or patch or island. Local bonds of balloon 51 to catheter shaft 35, 45 are arranged in a pattern that allows flow to inflate unbonded portion of balloon. Adhesive 54 attaches stent 52 to band 56b, 56c and may be comprised of biodegradable or dissolvable materials such as poly lactic acid (PLA), poly glycolic acid (PGA), or poly lactic glycolic acid (PLGA), or may be comprised of EVA, polyurethane, nylon, or other materials. In some embodiments adhesive extends into openings through wall thickness of stent 52.

An exemplary method of using a stent 52 with implant delivery system 50 is now described. A guidewire is advanced into a patient's femoral artery using known techniques, through a patient's vessel and past a treatment site. Stent 52 (for example stent 10, 20, or other stent) is loaded onto stent delivery system 50 and introduced over the guidewire into the patient's vessel. The stent and stent delivery system combination is advanced over the guidewire and through the patients vessel until the stent is located at a treatment site, for example within a stenosis in a popliteal artery. Stent 52 is deployed by inflating balloon 51 thereby fracturing adhesive 54 attachments between band(s) 56a, 56b, 56c and stent 52, causing or allowing stent to expand. Catheter shaft 35, 45 is then withdrawn through the patient's vessel and out of the patient's body. In the case of biodegradable or dissolvable adhesive 54, any of adhesive that is pinned under stent 52, or which embolizes, dissolves or degrades over time. Stent 52 does not change length on deployment because the stent is immobilized on catheter shaft 35 during delivery to the treatment site and because there is no sheath to draw past the stent during deployment.

Figure 6A:
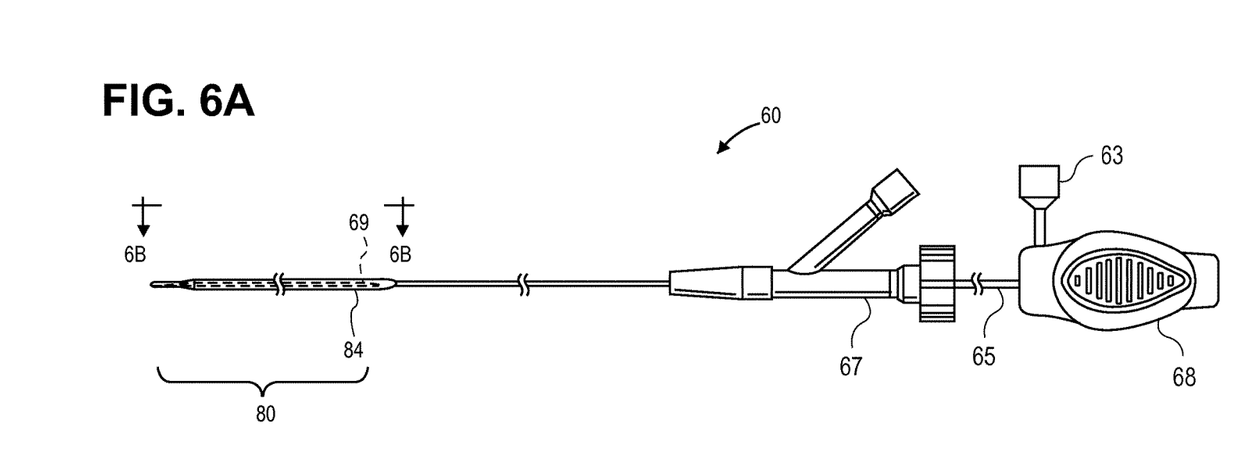
FIGS. 6A, 6B, 6C, 7, 8A, 8B, 8C and 8D illustrate schematic side views of implant delivery systems having features in accordance with the principles of the present disclosure.
Figure 6B:
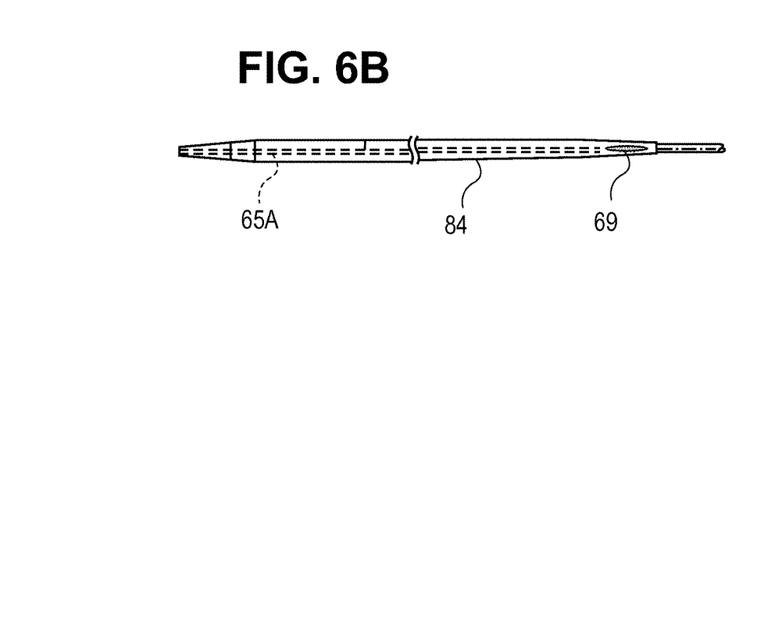
Figure 6C:
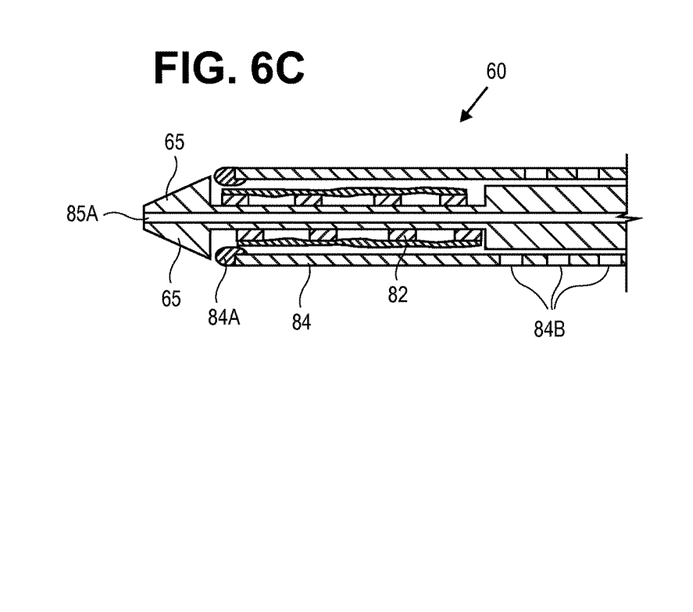
Figure 7:
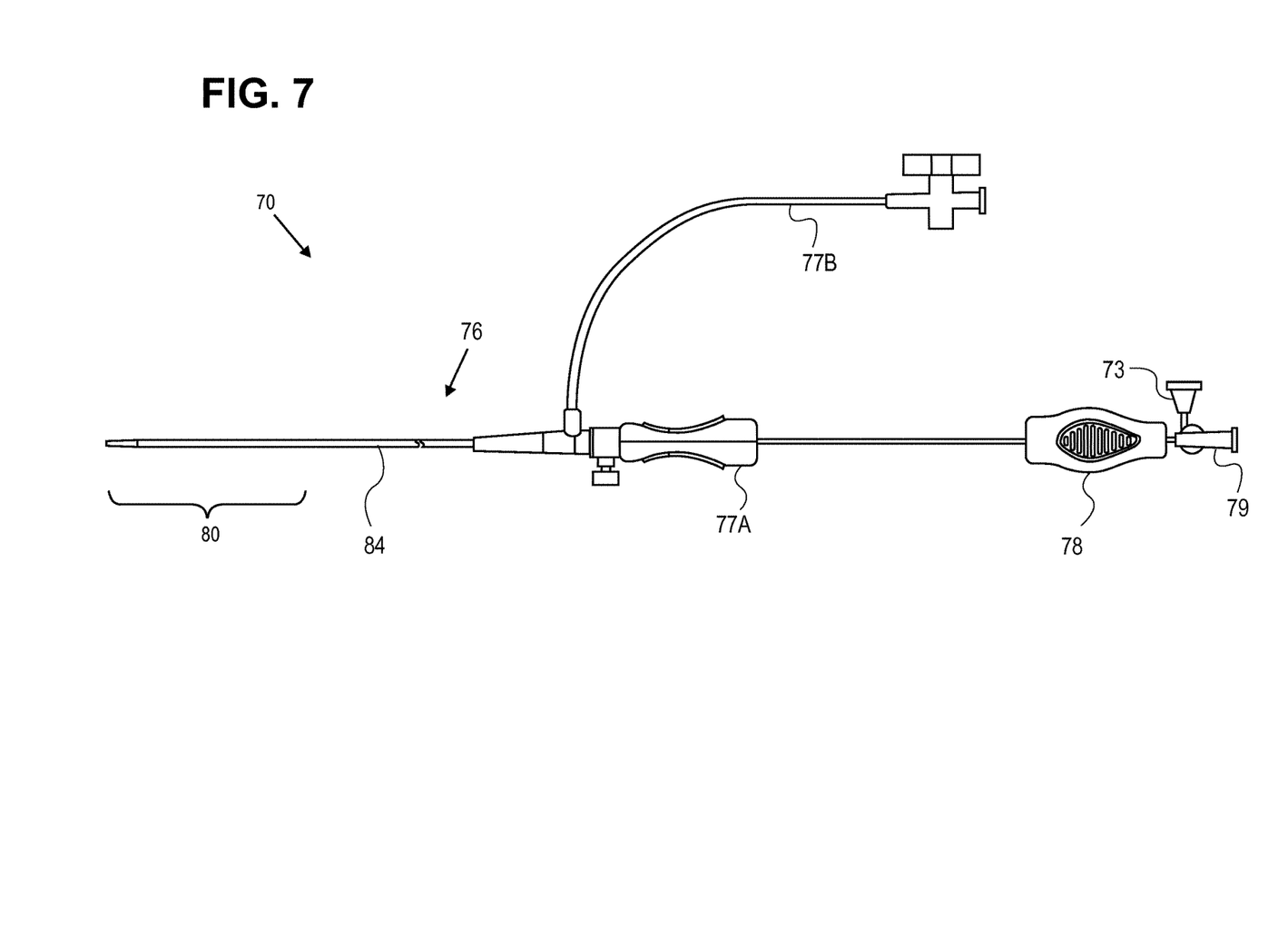

FIGS. 6A, 6B, 8A, 8B, 8C and 8D illustrate RX delivery system 60 comprised of implant delivery catheter 66 having distal region 80 and stent 82. Implant delivery catheter 66 includes catheter shaft 65, guidewire lumen 65a, proximal guidewire exit skive 69, proximal handle 68, sheath 84 and distal manifold 67. Proximal handle 68 is sealingly attached to catheter shaft 65 and may be comprised of polycarbonate. Catheter shaft 65 is relatively flexible, may be comprised of a polymeric material such as nylon or PEBAX, and may range in length from 60 cm to 300 cm. Catheter outside diameter may range from about 2 Fr to about 10 Fr. Guidewire lumen 65a diameter may be large enough to allow passage of guidewires ranging in diameter from 0.009" to 0.038". Distal manifold 67 is sealingly attached to sheath 84 and may be comprised of polycarbonate. Sheath 84 may be comprised of braid-reinforced polyester, non-reinforced polymers such as nylon or polyester, or other materials, and adapted to resist kinking and to transmit axial forces along its length. Sheath 84 may be constructed so as to have varying degrees of flexibility along its length. In one embodiment (FIG. 6C) sheath 84 includes seal 84a, weep holes 84b, or both. Seal prevents liquids and body fluids from contacting stent 82 when sheath is fully advanced to cover stent 82, and may be constructed of elastomeric materials such as low durometer PEBAX, polyurethane, or other materials. Weep holes 84b allow annular space between sheath 84 and catheter shaft 65 to be purged of air. Stent 82 may be comprised of stent 10, 20, or other stents. In some embodiments, coating 14 or shell 24 is substantially shielded from dissolution or biodegradation causing media due to barrier properties of sheath in combination with sheath seal.

Optionally, implant delivery catheter 66 is further comprised of balloon 81 (FIG. 8D), balloon inflation lumen within catheter 65 (not shown), and balloon inflation hub 63. Hub 63 is sealingly attached to proximal handle 88, is adapted to reversibly connect to other medical devices (for example by means of a luer fitting) and may be comprised of polycarbonate. Balloon 81 is sealingly attached at both proximal and distal ends to catheter shaft 65 and may be comprised of biaxially oriented nylon, polyester, Pebax, polyolefin, or other materials. In one embodiment, balloon 81 is constructed such that the coefficient of friction of the balloon in contact with stent 82 is greater than the coefficient of friction of sheath 84 in contact with stent 82.

FIGS. 7, 8A, 8B, 8C and 8D illustrate OTW delivery system 70 comprised of implant delivery catheter 76 having distal region 80 and stent 82. Implant delivery catheter 76 includes catheter shaft 75, guidewire lumen (not shown), proximal guidewire exit port 79, proximal handle 78, sheath 84 and distal manifold 77a. Sheath 84 may optionally be comprised of seal 84a, weep holes 84b, or both and distal manifold 77a includes infusion tube with stopcock 77b. Catheter shaft 75, guidewire lumen, proximal handle 78 and distal manifold have substantially the same construction, dimensions, and function as catheter shaft 65, guidewire lumen 65a, proximal handle 68 and distal manifold 67 described above in conjunction with FIGS. 6A to 6D. Stent 82 may be comprised of stent 10, 20, or other stents. In some embodiments, coating 14 or shell 24 is substantially shielded from dissolution or biodegradation causing media due to barrier properties of sheath in combination with sheath seal.

Optionally, implant delivery catheter 76 is further comprised of balloon 81 (FIG. 8D), balloon inflation lumen within catheter 75 (not shown), and balloon inflation hub 73. Hub 73 is sealingly attached to proximal guidewire exit port 79, is adapted to reversibly connect to other medical devices (for example by means of a luer fitting) and may be comprised of polycarbonate. Balloon 81 is sealingly attached at both proximal and distal ends to catheter shaft 75 and may be comprised of biaxially oriented nylon, polyester, Pebax, polyolefin, or other materials.

Figure 8A:
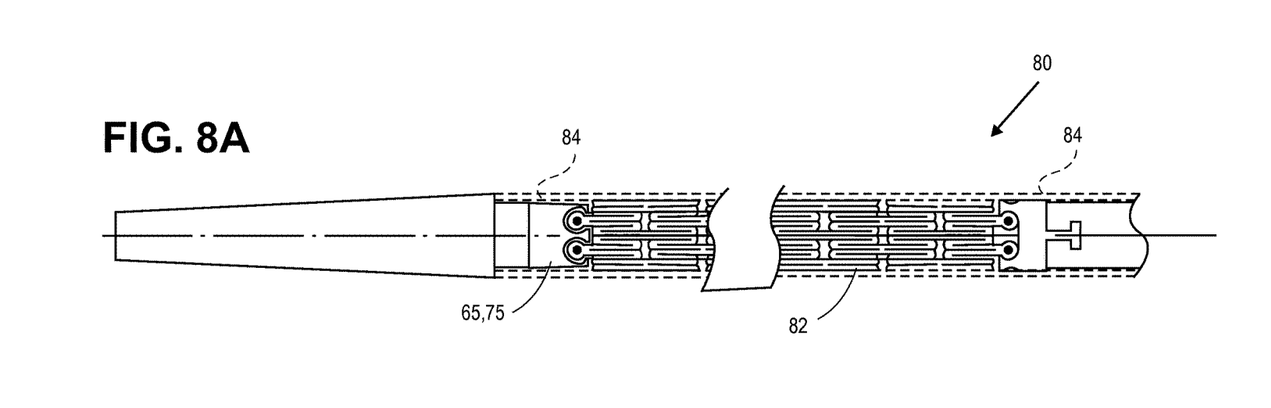
Figure 8B:
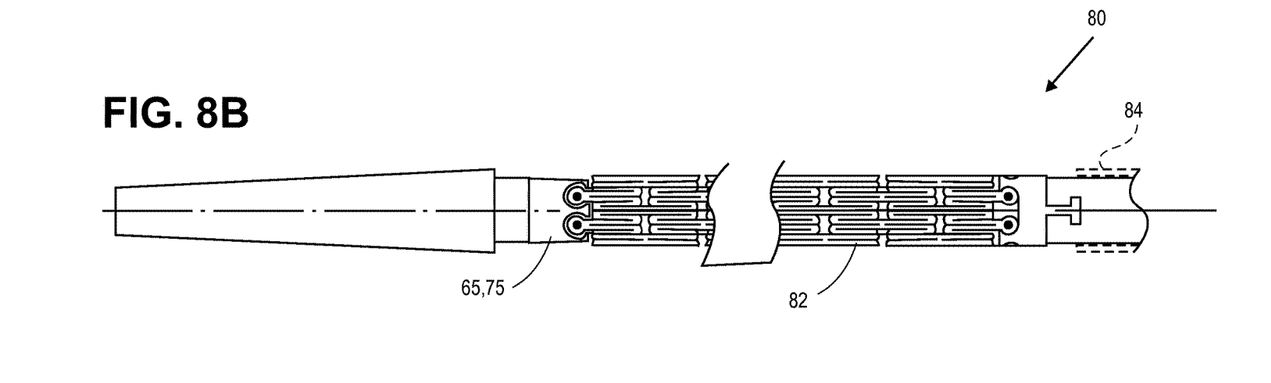
Figure 8C:
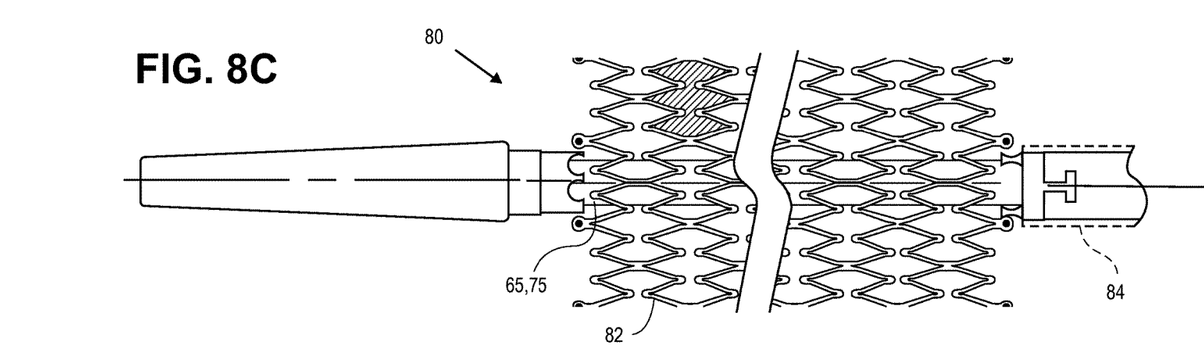

An exemplary method of using implant delivery system 60, 70 with stent 82 is now described with the assistance of FIGS. 8A to 8C. A guidewire is advanced into a patient's femoral artery using known techniques, through a patient's vessel and past a treatment site. Stent 82 (for example stent 10, 20) is loaded onto stent delivery system 60, 70 (FIG. 8A) and introduced over the guidewire into the patient's vessel. The stent and stent delivery system combination is advanced over the guidewire and through the patients vessel until the stent is located at a treatment site, for example within a stenosis in an iliac artery. Stent 82 is deployed by sliding proximal handle 68, 78 and distal manifold 67, 77a closer together, thereby causing sheath 84 to withdraw proximally and uncover stent 82 (FIG. 8B). Withdrawal of sheath from stent 10, 20 allows blood and/or media to contact coating or shell thereby releasing stent restraint after dissolution or biodegradation of coating or shell, allowing stent to self-expand (FIG. 8C). Catheter 66, 76 is then withdrawn through the patient's vessel and out of the patient's body. Because the coating or shell restrains the stent from expanding or changing length sheath withdrawal force is reduced and the stent does not change length on deployment.

In some methods, sheath 84 is partially withdrawn from stent 82 so as to allow uncovered portion of stent to expand into contact with the vessel wall, thereby providing frictional localization of the expanded portion of the stent against the vessel wall.

In some embodiments, before dissolution or biodegradation of coating or shell an operator can advance the sheath distally so as to recapture the stent. This is possible because the coating or shell provides a smooth covering over the structural portion of the stent such that the distal end of the sheath will not become mechanically entangled with the structural portion. Recapture of a stent is desirable when the operator wishes to change the eventual deployed position of the stent or for other reasons. In other embodiments, sheath seal 84a prevents blood and/or media to contact stent 82 during stent delivery in the patient, thereby preventing expansion of stent 82 secondary to premature dissolution or biodegradation of coating 14 or shell 24. In still other embodiments, prior to introduction into a patient delivery system 60, 70 is flushed with fluid to purge air by connecting a syringe filled with flushing solution (e.g. saline) to distal manifold 67, 77a and forcing flushing solution through sheath 84 and out weep holes 84b, thereby preventing flushing fluid from contacting stent 82 and potentially causing premature dissolution or biodegradation of coating 14 or shell 24.

In methods of using embodiments of implant delivery system 60, 70 where balloon 81 is incorporated into the system, balloon 81 is inflated after withdrawal of sheath 84 (FIG. 8D) by connecting inflation device (not shown) to hub 63, 73 and pressurizing balloon inflation lumen with fluid or gas thereby causing stent 82 to expand after fracture or compromise of coating or shell. In some embodiments stent 82 is fully expanded into contact with vessel wall by expansion of balloon. Because the coating or shell restrains the stent from expanding or changing length and because the stent is expanded by balloon, sheath withdrawal force is reduced and the stent does not change length on deployment.

Figure 8D:
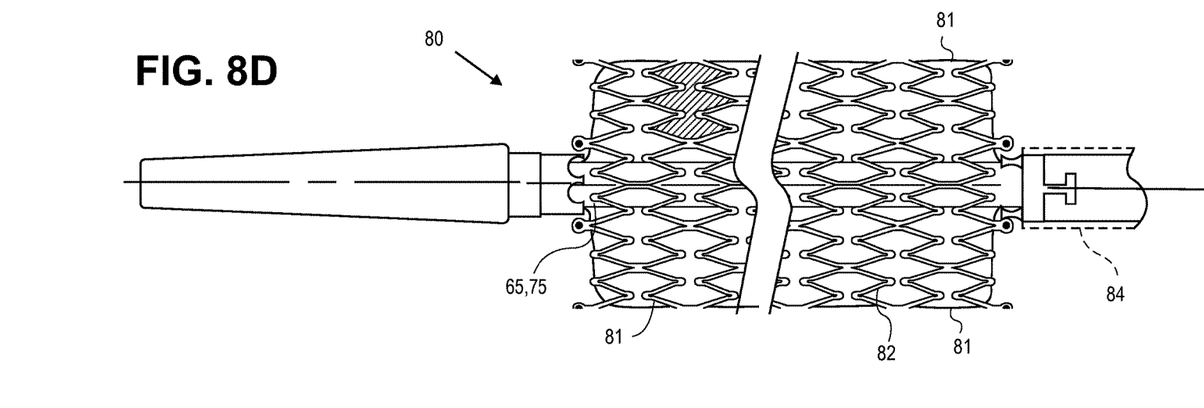

An alternate exemplary method of using embodiments of implant delivery system 60, 70 where balloon 81 is incorporated into the system with stent 82 is now described with the assistance of FIGS. 8A to 8D. A guidewire is advanced into a patient's femoral artery using known techniques, through a patient's vessel and past a treatment site. Stent 82 (for example any stent that self expands when not restrained by another device or component) is loaded onto stent delivery system 60, 70 (FIG. 8A) and introduced over the guidewire into the patient's vessel. The stent and stent delivery system combination is advanced over the guidewire and through the patients vessel until the stent is located at a treatment site, for example within a stenosis in a carotid artery. Balloon 81 is inflated prior to withdrawal of sheath 84 (FIG. 8A, balloon not shown) by connecting inflation device (not shown) to hub 63, 73 and pressurizing balloon inflation lumen with fluid or gas until sliding friction of stent 82 against balloon 81 exceeds sliding friction of stent 82 against sheath 84. Stent 82 is deployed by sliding proximal handle 68, 78 and distal manifold 67, 77a closer together, thereby causing sheath 84 to withdraw proximally and uncover stent 82 (FIG. 8D). Catheter 66, 76 is then withdrawn through the patient's vessel and out of the patient's body. Because the inflated balloon restrains the stent from changing length (for example buckling, stretching, kinking, or "bunching up") in the sheath, sheath withdrawal force is reduced and the stent does not change length on deployment.

While the various examples of the present invention have related to stents and stent delivery systems, the scope of the present invention is not so limited. For example, while particularly suited for stent delivery systems, it will be appreciated that the various aspects of the present invention are also applicable to systems for delivering other types of expandable implants. By way of non-limiting example, other types of expanding implants include anastomosis devices, blood filters, grafts, vena cava filters, percutaneous valves, aneurism treatment devices, or other devices.

It has been shown how certain objects of the invention have been attained in a preferred manner. Modifications and equivalents of the disclosed concepts are intended to be included within the scope of the claims. Alternate materials for many of the delivery system components are generally well known in the art can be substituted for any of the non-limiting examples listed above provided the functional requirements of the component are met. Further, while choices for materials and configurations may have been described above with respect to certain embodiments, one of ordinary skill in the art will understand that the materials and configurations described are applicable across the embodiments.

What is claimed is:

1. An implant delivery system comprising:
   a catheter shaft;
   a stent mounted on the catheter shaft, the stent including a scaffold having a collapsed configuration and an expanded configuration;
   a shell surrounding the scaffold, the shell being configured to retain the scaffold in the collapsed configuration, the shell comprising tubing into which the scaffold is inserted, the shell being formed of a material that dissolves upon exposure to a dissolution media, and the scaffold being expandable from the collapsed configuration to the expanded configuration through exposure of the shell to the dissolution media, wherein the shell comprises perforations configured to assist fracture of the shell upon expansion of the scaffold; and
   a tubular sheath covering, and in contact with, the shell while the scaffold is in the collapsed configuration, the tubular sheath being movable to expose the shell and enable the scaffold to expand from the collapsed configuration to the expanded configuration after at least a portion of the shell dissolves upon exposure to the dissolution media.

2. The implant delivery system of claim 1, wherein the shell comprises at least one of preplaced slits or slots configured to assist fracture of the shell upon expansion of the scaffold.

3. The implant delivery system of claim 2, wherein the shell comprises the preplaced slits, and wherein at least one of the preplaced slits is a longitudinal slit.

4. The implant delivery system of claim 1, wherein the shell forms a smooth exterior surface over the scaffold.

5. The implant delivery system of claim 1, wherein the scaffold is self-expanding.

6. The implant delivery system of claim 5, wherein the scaffold is configured to self-expand to the expanded configuration as the shell dissolves.

7. The implant delivery system of claim 1, wherein the scaffold is balloon-expandable.

8. The implant delivery system of claim 7, further comprising a balloon interposed between the scaffold and the catheter shaft, wherein the balloon is configured to expand the scaffold to the expanded configuration as the shell dissolves.

9. The implant delivery system of claim 1, wherein the shell is configured to maintain the scaffold in the collapsed configuration, and wherein the scaffold has an unexpanded diameter and a fixed length in the collapsed configuration.

10. The implant delivery system of claim 1, wherein the tubular sheath is axially slidable relative to the stent.

11. The implant delivery system of claim 1, wherein the shell comprises one or more antirestenotic agents.

12. The implant delivery system of claim 1, wherein the shell comprises an anti-inflammatory agent.

13. The implant delivery system of claim 1, wherein the shell comprises an antiatheromatic agent.

14. The implant delivery system of claim 1, wherein the shell comprises an antioxidative agent.

15. The implant delivery system of claim 1, further comprising a sheath seal configured to prevent the dissolution media from contacting the shell until the tubular sheath is moved to expose the shell to the dissolution media.

16. An implant delivery system comprising:
a catheter shaft;
a stent mounted on the catheter shaft, the stent including a scaffold having a collapsed configuration and an expanded configuration;
a shell surrounding the scaffold, the shell being configured to retain the scaffold in the collapsed configuration, the shell comprising a film wrapped around the scaffold, the shell being formed of a material that dissolves upon exposure to a dissolution media, and the scaffold being expandable from the collapsed configuration to the expanded configuration through exposure of the shell to the dissolution media, wherein the shell comprises perforations configured to assist fracture of the shell upon expansion of the scaffold; and
a tubular sheath covering, and in contact with, the shell while the scaffold is in the collapsed configuration, the tubular sheath being movable to expose the shell and enable the scaffold to expand from the collapsed configuration to the expanded configuration after at least a portion of the shell dissolves upon exposure to the dissolution media.

17. The implant delivery system of claim 16, wherein the shell comprises at least one of preplaced slits or slots configured to assist fracture of the shell upon expansion of the scaffold.

18. The implant delivery system of claim 16, wherein the scaffold is self-expanding.

19. The implant delivery system of claim 16, wherein the scaffold is balloon-expandable.

20. The implant delivery system of claim 16, wherein the shell comprises at least one of: an antirestenotic agent, an anti-inflammatory agent, an antiatheromatic agent, or an antioxidative agent.

21. The implant delivery system of claim 16, further comprising a sheath seal configured to prevent the dissolution media from contacting the shell until the tubular sheath is moved to expose the shell to the dissolution media.

22. An implant delivery system comprising:
a catheter shaft;
a stent mounted on the catheter shaft, the stent including a scaffold having a collapsed configuration and an expanded configuration;
a shell surrounding the scaffold, the shell being configured to retain the scaffold in the collapsed configuration, the shell comprising tubing into which the scaffold is inserted, the shell being formed of a material that dissolves upon exposure to a dissolution media, and the scaffold being expandable from the collapsed configuration to the expanded configuration through exposure of the shell to the dissolution media, wherein the shell comprises local thinning of a wall thickness that assists fracture of the shell upon expansion of the scaffold; and
a tubular sheath covering, and in contact with, the shell while the scaffold is in the collapsed configuration, the tubular sheath being movable to expose the shell and enable the scaffold to expand from the collapsed configuration to the expanded configuration after at least a portion of the shell dissolves upon exposure to the dissolution media.

23. The implant delivery system of claim 22, further comprising a sheath seal configured to prevent the dissolution media from contacting the shell until the tubular sheath is moved to expose the shell to the dissolution media.

* * * * *